(12) United States Patent
Ahn et al.

(10) Patent No.: US 11,655,279 B2
(45) Date of Patent: *May 23, 2023

(54) METHOD FOR PRODUCING ACTIVE FORM OF LONG-ACTING INSULIN ANALOGUE DERIVATIVE USING CLOSTRIPAIN

(71) Applicant: DAEWOONG PHARMACEUTICAL CO., LTD., Gyeonggi do (KR)

(72) Inventors: Kyong Hoon Ahn, Seoul (KR); Seonkyeong Jeong, Gyeonggi-do (KR); Chaeha Yoon, Gyeonggi-do (KR)

(73) Assignee: DAEWOONG PHARMACEUTICAL CO., LTD., Gyeonggi-do (KR)

( * ) Notice: Subject to any disclaimer, the term of this patent is extended or adjusted under 35 U.S.C. 154(b) by 231 days.

This patent is subject to a terminal disclaimer.

(21) Appl. No.: 17/266,580

(22) PCT Filed: Jul. 19, 2019

(86) PCT No.: PCT/KR2019/008958
§ 371 (c)(1),
(2) Date: Feb. 6, 2021

(87) PCT Pub. No.: WO2020/032423
PCT Pub. Date: Feb. 13, 2020

(65) Prior Publication Data
US 2021/0309710 A1    Oct. 7, 2021

(30) Foreign Application Priority Data
Aug. 8, 2018  (KR) .................. 10-2018-0092244

(51) Int. Cl.
*C07K 14/62* (2006.01)
*C07K 14/76* (2006.01)

(52) U.S. Cl.
CPC .............. *C07K 14/62* (2013.01); *C07K 14/76* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 5,728,543 A * | 3/1998 | Dorschug | C07K 14/62 435/68.1 |
| 6,841,361 B1 | 1/2005 | Oka et al. | |
| 10,155,792 B2 * | 12/2018 | Ekblad | C07K 14/195 |
| 2021/0300984 A1 * | 9/2021 | Ahn | C07K 14/62 |

FOREIGN PATENT DOCUMENTS

| EP | 0195691 A1 | 9/1986 |
|---|---|---|
| KR | 1020017013921 A | 4/2000 |
| KR | 1020150058454 A | 5/2015 |
| KR | 1020150087130 A | 7/2015 |
| KR | 1020150138101 A | 12/2015 |
| RU | 2062301 C1 | 6/1996 |
| RU | 2495131 C2 | 10/2013 |
| RU | 2524150 C2 | 7/2014 |
| WO | 2014048977 A1 | 4/2014 |

OTHER PUBLICATIONS

Wan et al.,"Diabetes-Associated Mutations in Human Insulin: Crystal Structure and Photo-Cross-Linking Studies of A-Chain Variant Insulin Wakayama", Biochemistry 44: 5000-5016 (Year: 2005).*
Duttaroy, A., et al., "Development of a Long-Acting Insulin Analog Using Albumin Fusion Technology", "Diabetes", Jan. 2005, vol. 54.
Mayer, J.P., et al., "Insulin Structure and Function", PeptideScience, 2007, pp. 687-713, vol. 88, No. 5, Publisher: Wiley InterScience.
Chen, X.,, et al., "Fusion Protein Linkers: Property, Design, and Funcationality", Adv Drug Deliv Rev, 2014, pp. 1357-1369, vol. 65, No. 10, Publisher: NIH Public Access.
Dedova, I.I., "Insulin Therapy Manual for Doctors", Ministry of Health of the Russian Federation, 2004, Publisher: www.voed.ru/insulinotherapy.htm.
Dedova, I.I., "Insulin Therapy Manual for Doctors", Ministry of Health of the Russian Federation, 2004, Page(s) Eng Trans, Publisher: www.voed.ru/insulinotherapy.htm.
Katsoyannis, P., et al., "A synthetic human insulin analogue modified at position B22. [Lys22-b] human insulin", Journal of the Chemical Society, Perkin Transactions 1, 1975, p. 1, vol. 5.
Maeda, Y., et al., "Engineering of Functional Chimeric Protein G-Vargula Luciferase", Analytical Biochemistry, 1997, pp. 147-152, vol. 249, No. AB972181, Publisher: Academic Press.
Orlando, M., "Modification of proeins and low molecular weight substances with hydroxyethyl starch (HES)", Biotechnologie-Gesellschaft Mittelhesen mbH, 2003, Publisher: Justus-Liebig-Universitat Giessen.
Pakula, A., et al., "Genetic Analysis of Protein Stability and Function", Annu. Rev. Genet., 1898, pp. 289-310, vol. 23.

(Continued)

*Primary Examiner* — Anand U Desai
(74) *Attorney, Agent, or Firm* — Hultquist, PLLC; Steven J. Hultquist

(57) ABSTRACT

The present invention relates to a method for producing an active form of a long-acting insulin analogue derivative, in which the amino acid at position 22 of the insulin B-chain is substituted from arginine (Arg) to lysine (Lys), so that the insulin analogue can be converted to an active form without cleavage of the B-chain even when it is reacted with clostripain. In a conventional method of converting proinsulin to an active form by use of trypsin, an albumin binding domain is cleaved, making it difficult to convert the long-acting insulin analogue derivative to an active form. The production method according to the present invention overcomes this difficulty, and thus it can be effectively used for the production of a long-acting therapeutic agent for treatment of diabetes.

18 Claims, 12 Drawing Sheets
(11 of 12 Drawing Sheet(s) Filed in Color)
Specification includes a Sequence Listing.

(56) References Cited

OTHER PUBLICATIONS

Schilling, RJ, et al., "Degradation of insulin by trypsin and alphachymotrypsin", Pharm Res., 1991, pp. 721-727, vol. 8, No. 6, Publisher: PubMed.

Tokuriki, N., et al., "Stability effects of mutations and protein evolvability", Structural Biology, 2009, pp. 596-604, vol. 19, Publisher: Elsevier.

Weitzel, G., et al., "Structure and activity of insulin, XV [1-5], Further evidence for the importance of arginine residue B22 in the activity of insulin. Semisyntheses of despentapeptide-(B23-30)-insulins varied in B22 using desnonapeptide (B22-30)-insulin and tetrapeptides", Chemistry Medicine, 1977, Page(s) DOI: 10.1515/BCHM2.1977.358.2.1573, Publisher: Semantic Scholar.

Zhou, J., et al., "Preparation and PEGylation of exedin-4 peptide secreted from yeast Pichia pastoris", European Journal of Pharmaceutics and Biopharmaceutics, 2009, pp. 412-417, vol. 72, Publisher: Elsevier.

* cited by examiner

METHOD FOR PRODUCING ACTIVE FORM OF LONG-ACTING INSULIN ANALOGUE DERIVATIVE USING CLOSTRIPAIN

CROSS-REFERENCE TO RELATED APPLICATIONS

This application is a U.S. national phase under 35 USC § 371 of International Patent Application No. PCT/KR2019/008958 filed Jul. 19, 2019, which in turn claims priority under 35 USC § 119 of Korean Patent Application No. 10-2018-0092244 filed Aug. 8, 2018. The disclosures of International Patent Application No. PCT/KR2019/008958 and Korean Patent Application No. 10-2018-0092244 are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "554_SeqListing_ST25.txt" created on Feb. 6, 2021 and is 5,986 bytes in size. The sequence listing contained in this .txt file is part of the specification and is hereby incorporated by reference herein in its entirety.

TECHNICAL FIELD

The present invention relates to a method for producing an active form of a long-acting insulin analogue derivative using clostripain, and more particularly to method for producing an active form of a long-acting insulin analogue derivative, in which the amino acid at position 22 of the insulin B-chain is substituted from arginine (Arg) to lysine (Lys), so that the insulin analogue can be converted to an active form without cleavage of the B-chain even when it is reacted with clostripain.

BACKGROUND ART

Diabetes is a metabolic disease characterized by high glucose levels, and is developed by a combination of genetic and environmental factors. Diabetes includes type 1 diabetes, type 2 diabetes, gestational diabetes, and other states that cause hyperglycemia. Diabetes means a metabolic disorder in which the pancreas produces insufficient amounts of insulin or in which the human body's cells fail to respond appropriately to insulin, and thus their ability to absorb glucose is impaired. As a result, glucose builds up in the blood.

Type 1 diabetes, also called insulin-dependent diabetes mellitus (IDDM) and adolescent-onset diabetes, is caused by beta-cell destruction, leading to absolute insulin deficiency. On the other hand, type 2 diabetes, known as non-insulin dependent diabetes mellitus (NIDDM) and adult-onset diabetes, is associated with predominant insulin resistance and thus relative insulin deficiency and/or a predominantly insulin secretory defect with insulin resistance.

In particular, diabetes is associated with various complications such as cardiovascular disease and retinopathy, and thus is a disease that becomes very burdensome if proper management such as blood glucose control is not done. The world market for diabetes medications is expected to expand from $41.7 billion in 2015 to $66.1 billion by 2022, and is expected to be the second largest after the anticancer drug market. Globally, there are 422 million adults with diabetes in 2014, which is 8.5% of the total adult population, nearly double that of 4.5% in 1980 (WHO, 2016). In addition, the total global health expenditure due to diabetes is estimated at $673 billion, and the number of diabetic patients aged 20-79 is expected to increase to about 620 million by 2040.

The most representative treatment methods for treating diabetes include a method of administering insulin to control the blood glucose level of the patient to a normal level. Insulin is a blood glucose-regulating hormone that is secreted from the human pancreas. It functions to transfer excess glucose in the blood to cells to supply energy to the cells and maintain the blood glucose levels at normal levels.

Insulin undergoes various post-translational modifications along the production pathway. Production and secretion are largely independent; prepared insulin is stored awaiting secretion. Both C-peptide and mature insulin are biologically active.

In mammals, insulin is synthesized in pancreatic beta-cells. Insulin is composed of two polypeptide chains (A-chain and B-chain) which are linked to each other by disulfide bonds. However, insulin is first synthesized as a single polypeptide called preproinsulin in pancreatic beta-cells. The preproinsulin contains a 24-amino-acid signal peptide which directs the nascent polypeptide chain to the rough endoplasmic reticulum. The signal peptide is translocated into the lumen of the rough endoplasmic reticulum, and then cleaved, thus forming proinsulin. In the rough endoplasmic reticulum, the proinsulin is folded into the correct conformation, and three disulfide bonds are formed. 5 to 10 minutes after its assembly in the endoplasmic reticulum, the proinsulin is transported to the trans-Golgi network where immature granules are formed.

Proinsulin undergoes maturation into active insulin through the action of cellular endopeptidases known as prohormone convertases (PC1 and PC2), as well as carboxypeptidase E which is an exoprotease. The endopeptidases cleave at 2 positions, releasing a fragment called the C-peptide, and leaving 2 peptide chains, the B- and A-chains, linked by 2 disulfide bonds. The cleavage sites are each located after a pair of basic residues (lysine (Lys)-64 and arginine (Arg)-65, and arginine (Arg)-31 and arginine (Arg)-32). After cleavage of the C-peptide, these 2 pairs of basic residues are removed by the carboxypeptidase. The C-peptide is located in the central portion of proinsulin, and the primary sequence of proinsulin goes in the order of "B-C-A" (the B-chain and the A-chain were identified on the basis of mass, and the C-peptide was discovered later).

The resulting mature insulin (active insulin) is packaged inside mature granules waiting for metabolic signals (e.g., leucine (Leu), arginine (Arg), glucose and mannose) and vagal nerve stimulation to be exocytosed from the cell into the circulation.

For the treatment of diabetes, active insulin is administered. Technologies of producing active insulin using gene recombination technology are as follows. First, Eli Lilly Corp. employed a method which comprises the steps of: expressing an A-chain and a B-chain separately using *E. coli*, and mixing the A-chain and the B-chain in vitro to form disulfide bridges, thereby linking the A- and B-chains to each other via the disulfide bonds. However, this method had a problem in that the production efficiency is poor. Then, Eli Lilly Corp. has developed a method which comprises the steps of: expressing proinsulin; forming the disulfide bonds in vitro; and then cleaving out the C-peptide from the product with trypsin and carboxypeptidase B, thereby producing insulin.

Novo Nordisk Corp. has developed a method which comprises the steps of: expressing mini-proinsulin comprising a B-chain and an A-chain linked via two basic amino acids, in yeast; and then treating the mini-proinsulin with trypsin, producing insulin. This method has advantages in that disulfide bonds are formed during the expression and secretion of the mini-proinsulin and that the miniproinsulin is easily isolated and purified because it is secreted into a cultured medium. However, this method was difficult to apply to large-scale production comparable to production using E. coli.

Since then, the development of novel methods of producing insulin by gene recombination technology has been was made actively. Hoechst AG developed a method which comprises the steps of: expressing a novel insulin derivative or preproinsulin in E. coli; and forming disulfide bonds in vitro, followed by treatment with lysylendopeptidase or clostripain and carboxypeptidase B, thereby producing insulin. Bio-Technology General Corp. has developed a method in which a fusion protein comprising superoxide dismutase (SOD) linked with proinsulin is expressed in E. coli to increase the efficiency of expression and the efficiency of formation of disulfide bonds in vitro. Conversion of proinsulin into insulin was performed with trypsin and carboxypeptidase B. As described above, many methods of producing insulin by gene recombination technology have been attempted and improved in terms of the efficiency of expression, the efficiency of formation of disulfide bonds, and the process of conversion of proinsulin to insulin (KR 10-2001-7013921).

The present inventors have made extensive efforts to develop a production process suitable for a novel long-acting insulin analogue derivative developed by the present inventors, which has an increased in vivo half-life, resulting in an improvement in long-acting action compared to native insulin, and as a result, have found that the use of clostripain makes it possible to efficiently produce the novel long-acting insulin analogue derivative developed by the present inventors, thereby completing the present invention.

DISCLOSURE OF INVENTION

Technical Problem

It is an object of the present invention to provide a method for producing an active form of a novel long-acting insulin analogue derivative.

Technical Solution

To achieve the above object, the present invention provides a method for producing an active form of a long-acting insulin analogue derivative, the method comprising a step of reacting an insulin analogue derivative which comprises an insulin analogue comprising an insulin-B chain variant represented by the amino acid sequence of SEQ ID NO: 2, arginine (Arg) at amino acid position 22 of an insulin-B chain is substituted with lysine (Lys) in native insulin, and an albumin binding domain fused thereto, with clostripain.

The present invention also provides a long-acting insulin analogue derivative produced by the method.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
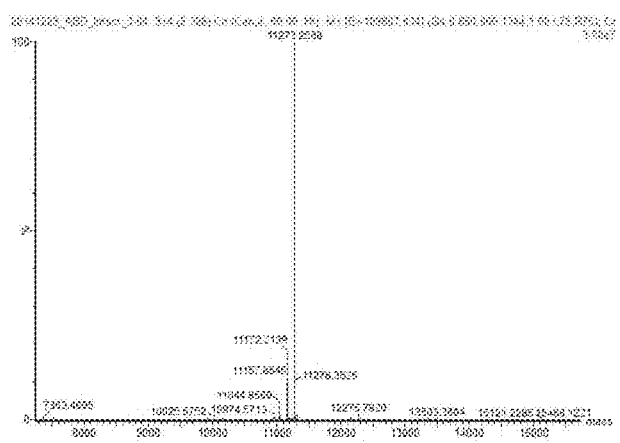
FIG. 1 shows the results of analyzing the stability of a long-acting insulin analogue derivative constructed by substituting arginine (Arg) at position 22 of the insulin B-chain with lysine (Lys) by treating with clostripain. Mass spectrometry indicated that when the insulin B-chain contained arginine (Arg) at position 22, cleavage thereof occurred, but when the arginine (Arg) was substituted with lysine (Lys), cleavage of the B-chain did not occur.

Unless otherwise defined, all technical and scientific terms used herein have the same meaning as commonly understood by one of ordinary skill in the art to which the present disclosure belongs. In general, the nomenclature used herein is well known and commonly used in the art.

An insulin analogue obtained by substituting one or more amino acids of native insulin has an increased in vivo half-life, and thus may be used as a basal insulin treatment agent. When this insulin analogue binds to albumin in the human body, the in vivo half-life thereof may further increase, so that the insulin analogue may be used as a weekly formulation.

The present inventors could find that when one or more amino acids of native insulin are substituted, the in vivo half-life of the insulin can be increased, and when an albumin binding domain is additionally fused thereto, the insulin can bind to albumin in vivo, and thus the half-life thereof can further increase. However, when the albumin binding domain was fused to an insulin analogue comprising one or more amino acid substitutions and when trypsin used in a conventional art was used in a process of converting the insulin analogue to an active form, a problem did arise in that cleavage of the albumin binding domain itself occurs, making it difficult to produce an active form lasting for a long time.

Accordingly, in the present invention, it was attempted to use clostripain as an enzyme that makes it possible to convert insulin to an active form without inducing cleavage of the albumin binding domain. However, clostripain induced cleavage of insulin itself, and for this reason, the amino acids of insulin were substituted, thereby preventing cleavage of the insulin itself.

Therefore, in one aspect, the present invention is directed to a method for producing an active form of a long-acting insulin analogue derivative, the method comprising a step of reacting an insulin analogue derivative in which an insulin analogue comprising an insulin-B chain variant represented by the amino acid sequence of SEQ ID NO: 2, arginine (Arg) at amino acid position 22 of an insulin-B chain is substituted with lysine (Lys) in native insulin, is fused to an albumin binding domain, with clostripain.

In the present invention, "an insulin analogue comprising an insulin-B chain variant represented by the amino acid sequence of SEQ ID NO: 2, arginine (Arg) at amino acid position 22 of an insulin-B chain is substituted with lysine (Lys) in native insulin" means that the insulin analogue may comprise further amino acid variant in insulin A chain or insulin B chain in addition to arginine (Arg)-to-lysine (Lys) substitution at amino acid position 22 of an native insulin B chain.

In the present invention, the insulin analogue may further comprise one or more amino acid substitutions selected from the group consisting of: a valine (Val)-to-leucine (Leu) substitution at amino acid position 3 of an insulin A-chain represented by the amino acid sequence of SEQ ID NO: 4; a threonine (Thr)-to-aspartic acid (Asp) substitution at amino acid position 8 of the insulin A-chain represented by the amino acid sequence of SEQ ID NO: 4; an isoleucine (Ile)-to-lysine (Lys) substitution at amino acid position 10 of the insulin A-chain represented by the amino acid sequence of SEQ ID NO: 4; a tyrosine (Tyr)-to-glutamic acid (Glu) substitution at amino acid position 14 of the insulin A-chain represented by the amino acid sequence of SEQ ID NO: 4; a tyrosine (Tyr)-to-phenylalanine (Phe) substitution at amino acid position 19 of the insulin A-chain represented by the amino acid sequence of SEQ ID NO: 4; a histidine (His)-to-threonine (Thr) substitution at amino acid position 5 of an insulin B-chain variant represented by the amino acid sequence of SEQ ID NO: 2; a serine (Ser)-to-aspartic acid (Asp) substitution at amino acid position 9 of the insulin B-chain variant represented by the amino acid sequence of SEQ ID NO: 2; a glutamic acid (Glu)-to-alanine (Ala) substitution at amino acid position 13 of the insulin B-chain variant represented by the amino acid sequence of SEQ ID NO: 2; a leucine (Leu)-to-glutamine (Gln) substitution at amino acid position 17 of the insulin B-chain variant represented by the amino acid sequence of SEQ ID NO: 2; and a phenylalanine (Phe)-to-serine (Ser) substitution at amino acid position 24 of the insulin B-chain variant represented by the amino acid sequence of SEQ ID NO: 2, but is not limited thereto.

In an example of the present invention, the albumin-binding domain may comprise an albumin-binding motif represented by the following amino acid sequence:
GVSDFYKKLIX$_a$KAKTVEGVEALKX$_b$X$_c$I
wherein
X$_a$ is independently selected from D and E,
X$_b$ is independently selected from D and E, and
X$_c$ is independently selected from A and E.

In an example of the present invention, X$_a$ is D, X$_b$ is D, and X$_c$ is A.

In an embodiment of the present invention, the albumin-binding domain may comprise the following amino acid sequence:
LAX$_3$AKX$_6$X$_7$ANX$_{10}$ELDX$_{14}$Y-[BM]-LX$_{43}$X$_{44}$LP
wherein
[BM] is the albumin-binding motif as defined in the foregoing paragraph,
X$_3$ is independently selected from C, E, Q, and S;
X$_6$ is independently selected from C, E, and S;
X$_7$ is independently selected from A and S;
X$_{10}$ is independently selected from A, R, and S;
X$_{14}$ is independently selected from A, C, K, and S;
X$_{43}$ is independently selected from A and K; and
X$_{44}$ is independently selected from A, E, and S.

The albumin-binding domain may be represented by the amino acid sequences selected from the group consisting of SEQ ID NOS: 6 to 13, but is not limited thereto. The albumin-binding domain may preferably be represented by an amino acid sequence of SEQ ID NO: 6.

In the present invention, it is preferable that the albumin binding domain is fused to C-terminus of A-chain in insulin or insulin analogue of B-chain-C-chain-A-chain in terms of protein refolding efficiency, enzyme reaction efficiency and activity of the produced insulin derivative or insulin analogue derivatives. In this, a linker may be introduced between the insulin (or insulin analogue) and the albumin binding domain.

In the present invention, the polynucleotide encoding the insulin analogue and the nucleotide encoding the albumin binding domain may be introduced into the recombinant vector so that the insulin analogue and the albumin binding domain can be expressed as a fusion protein.

The function of the insulin analogue derivative according to the present invention varies depending on the three-dimensional structure of the derivative. Thus, it is possible to make small changes in the amino acid sequence of the long-acting insulin analogue derivative according to the present invention without affecting the function of the derivative. Therefore, the present invention includes variants of the albumin-binding domain or the long-acting insulin analogue derivative, which retain an albumin binding property or high resistance to enzymatic cleavage. For example, amino acid residues belonging to a specific functional group of amino acid residues (e.g., hydrophobicity, hydrophilicity, polarity, etc.) may be replaced with other amino acid residues belonging to the same functional group.

As used herein, the terms "albumin binding" and "binding affinity for albumin" refer to the property of a polypeptide or protein which may be tested by the use of surface plasmon resonance technology, such as a Biacore instrument. For example, albumin binding affinity may be tested in an experiment in which albumin or a fragment of thereof is immobilized on a sensor chip of the instrument, and a sample containing a polypeptide or protein to be tested is passed over the chip.

Alternatively, a polypeptide or protein to be tested is immobilized on a sensor chip of the instrument, and a sample containing albumin or a fragment thereof is passed over the chip. In this regard, the albumin may be serum albumin of mammalian origin, such as human serum albumin. Those skilled in the art may interpret the results obtained by such experiments to establish a quantitative measure of the binding affinity of the polypeptide or protein for albumin. If a quantitative measure is desired, for example to determine a $K_D$ value for the interaction, surface plasmon resonance methods may also be used. Binding values may for example be defined in a Biacore 2000 instrument (Biacore AB). Albumin is suitably immobilized on a measurement sensor chip, and samples of a polypeptide or protein whose affinity is to be determined are prepared by serial dilution and injected in random order. $K_D$ values may then be calculated from the results using, for example, the 1:1 Langmuir binding model of the BIAevaluation 4.1 software provided by the instrument manufacturer.

In one embodiment of the present invention, albumin to which the insulin analogue derivative binds is selected from among human serum albumin, rat serum albumin, cynomolgus serum albumin, and mouse serum albumin, but is not limited thereto.

In one specific embodiment, albumin to which the insulin analogue derivative binds is human serum albumin.

In the meantime, the description of the albumin-binding motif and the albumin-binding domain (or albumin-binding polypeptide) is construed to include the content disclosed in Korean Patent Laid-Open Publication No. 10-2015-0058454 corresponding to WO 2014048977.

The insulin analogue and the albumin-binding domain are linked to each other by a peptide bond; a polypeptide linker; or a non-peptidyl linker selected from the group consisting of polyethylene glycol, polypropylene glycol, an ethylene glycol-propylene glycol copolymer, polyoxyethylated polyol, polyvinyl alcohol, polysaccharides, dextran, polyvinyl ethyl ether, biodegradable polymers, fatty acids, nucleotides, lipid polymers, chitin, hyaluronic acid, and combinations thereof, but are not limited thereto.

In the present invention, a linker consisting of a repeat of $(GGGGS)_n$ (wherein n is an integer ranging from 1 to 6) sequence may be inserted between the insulin analogue and the albumin-binding domain. This is based on experimental results indicating that when the linker was not introduced, the refolding yield was low, but when two or more repeats of the (GGGGS) sequence were introduced, there was no significant difference in the refolding yield. Meanwhile, as the number (n) of repeats of the sequence increased, the rate of conversion to an active form of insulin by clostripain increased, but the in vivo pharmacokinetics of the insulin analogue was not significantly influenced. Taking the above-described results together, the linker preferably consists of 2 to 4 repeats of the GGGGS sequence.

Therefore, in the present invention, the insulin analogue and the albumin-binding domain can be linked to each other by the polypeptide linker, and the polypeptide linker may comprise $(GGGGS)_n$ (wherein n is an integer ranging from 1 to 6, but is not limited thereto). Preferably, the polypeptide linker may be represented by an amino acid sequence of SEQ ID NO: 5.

In the present invention, a reducing agent may be added during the reaction with clostripain. The reducing agent may be selected from the group consisting of cysteine, β-mercaptoethanol, TCEP, GSH, and DTT, but is not limited thereto. As the reducing agent, 0.1 to 0.5 mM of DTT is preferably added. More preferably, 0.1 to 0.4 mM of DTT is added.

The DTT may be added only once at an initial stage in which the insulin analogue derivative reacts with clostripain, that is, at the time point at which the reaction is initiated, and the DTT may additionally be added 2 to 5 times after it is added at the time point at which the reaction is initiated. However, it is most preferable in view of the convenience and efficiency of the production process that the DTT be added in the initial stage of the reaction of the insulin analogue derivative with clostripain and be further added at 3 to 6 hours after the reaction. The clostripain may be added at a concentration of 0.1 to 5 units, preferably 0.5 to 2 units, per mg of the protein, but is not limited thereto.

In the present invention, the insulin analogue derivative may further be reacted with carboxypeptidase B (CpB) which is added during or after the reaction with clostripain. In this, CpB may be added together with clostripain when the reaction is initiated.

In the present invention, the clostripain and/or carboxypeptidase B (CpB) are/is reacted under the conditions of pH 6.0-9.0, preferably 6.5-7.5, and under the temperature conditions of 4-40° C., preferably 30-40° C., but not limited thereto.

The CpB may be added at a concentration of 0.001 to 1 units, preferably 0.001 to 0.1 units, per mg of the protein, but is not limited thereto.

In another aspect, the present invention is directed to an active form of insulin analogue derivative produced by the above-described method.

In the present invention, the insulin analogue derivative may be produced in a recombinant microorganism into which the recombinant vector comprising a polynucleotide encoding the analogue derivative, by lysing and purifying the cultured recombinant microorganism.

The recombinant vector according to the present invention may be constructed as a vector for conventional cloning or expression, and may be constructed as a vector to use a prokaryotic or eukaryotic cell as a host cell.

As used herein, the term "vector" refers to a recombinant vector capable of expressing a target protein in an appropriate host cell, which is a gene construct including essential regulatory factors operably linked to enable the expression of a nucleic acid insert. The present invention can prepare a recombinant vector which includes a nucleic acid encoding an insulin analogue derivative thereof, and the insulin analogue derivative thereof of the present invention may be obtained via transformation or transfection of the recombinant vector into a host cell.

In the present invention, the nucleic acid encoding the insulin analogue and analogue derivative thereof is operably linked to a nucleic acid expression control sequence. As used herein, the term "operably linked" refers to a functional linkage between a nucleic acid expression control sequence (e.g., a promoter, a signal sequence, a ribosome-binding site, a transcription termination sequence, etc.) and another nucleotide sequence, and thus the control sequence can control the transcription and/or translation of the other nucleotide sequence.

As used herein, the term "promoter" refers to an untranslated nucleic acid sequence located upstream of a coding region, which includes a polymerase-binding site and has the activity of initiating transcription of a gene located downstream of the promoter into mRNA, i.e., a DNA site to which polymerase binds and initiates the transcription of a gene, and it is located at the 5' region of mRNA transcription initiation region.

For example, when the vector of the present invention is a recombinant vector, and a prokaryotic cell is used as a host cell, a strong promoter capable of promoting transcription (such as tac promoter, lac promoter, lacUV5 promoter, lpp promoter, pLλ promoter, pRλ promoter, racy promoter, amp promoter, recA promoter, SP6 promoter, trp promoter, trc promoter, phoA promoter, araBAD promoter, T5 promoter, and T7 promoter), a ribosome-binding site for initiation of translation, and a transcription/translation termination sequences are generally included.

Additionally, a vector that can be used in the present invention may be prepared by manipulating plasmids (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series, pPICZα series, pUC19, etc.), phages (e.g., λgt4λB, λ-Charon, λΔz1, M13, etc.), or viruses (e.g., SV40, etc.), which are commonly used in the art, but is not limited thereto.

Meanwhile, when the vector of the present invention is a recombinant vector, and a eukaryotic cell is used as a host cell, promoters derived from the genomes of mammalian cells (e.g., metallothionein promoter), promoters derived from mammalian viruses (e.g., adenovirus late promoter, 7.5K promoter of vaccinia virus, SV40 promoter, cytomegalovirus promoter, and tk promoter of HSV) may be used, and in general, the vector includes a polyadenylated sequence (e.g., a bovine growth hormone terminator and a polyadenylated sequence derived from SV40) as a transcription termination sequence.

In addition, the recombinant vector of the present invention includes an antibiotic resistance gene commonly used in the art as a selective marker, and may include, for example, genes having resistance to ampicillin, gentamicin, carbenicillin, chloramphenicol, streptomycin, kanamycin, geneticin, neomycin, and tetracycline.

The recombinant vector of the present invention may additionally include a different sequence to make it easy to purify target proteins being collected, i.e., insulin and/or an analogue thereof. The sequence to be additionally included may be a tag sequence for protein purification, e.g., glutathione S-transferase (Pharmacia, USA), a maltose-binding protein (NEB, USA), FLAG (IBI, USA), 6-histidine, etc., but the kinds of the sequence necessary for the purification of target proteins are not limited thereto. Fusion proteins expressed by the recombinant vector including the above tag sequence may be purified by affinity chromatography. For example, when glutathione S-transferase is fused, glutathione, which is the substrate of the enzyme, may be used, and when 6-histidine tag is used, a desired target protein may be easily collected by a Ni-NTA column. A recombinant microorganism transformed with the vector can be constructed using a recombinant vector comprising a polynucleotide encoding the insulin analogue and/or analogue derivative.

As used herein, the term "transformation" refers to a process of introducing DNA into a host cell and making the DNA replicable therein as a chromosomal factor or by completion of chromosomal integration, which is a phenomenon of artificially causing a genetic change by introducing exogenous DNA into a cell.

The method of transformation used in the present invention may be any transformation method, and it may be easily performed according to the conventional method used in the art. Examples of the commonly used transformation method may include a $CaCl_2$) precipitation method, the Hanahan method with improved efficiency using dimethyl sulfoxide (DMSO) as a reducing agent in the $CaCl_2$) precipitation method, electroporation, a $CaPO_4$ precipitation method, a protoplast fusion method, a stirring method using silicon carbide fiber, an agrobacteria-mediated transformation method, a transformation method using PEG, dextran sulfate-, lipofectamine-, and dry/suppression-mediated transformations, etc.

The method for transforming the recombinant vector including a nucleic acid encoding an insulin analogue and/or analogue derivative according to the present invention may not be limited to these methods, but any method for transformation or transfection commonly used in the art may be used without limitation.

A recombinant transformant of the present invention may be obtained by introducing a recombinant vector including a nucleic acid encoding an insulin analogue derivative into a host cell. An appropriate host to be used in the present invention may not be particularly limited as long as it can express the nucleic acid of the present invention. Examples of the appropriate host may include a bacteria belonging to the genus *Escherichia* such as *E. coli*, a bacteria belonging to the genus *Bacillus* such as *Bacillus subtilis*, a bacteria belonging to the genus *Pseudomonas* such as *Pseudomonas putida*, yeasts such as *Pichia pastoris, Saccharomyces cerevisiae*, and *Schizosaccharomyces pombe*, an insect cell such as *Spodoptera frugiperda* (SF9), and animal cells such as CHO, COS, and BSC, but is not limited thereto.

As used herein, the term "active form" means a mature form of an insulin, an insulin analogue or insulin analogue derivative capable of regulating blood glucose levels in vivo, and refers to an insulin, insulin analogue or insulin analogue derivative which is obtained by removing the C-peptide from the form of proinsulin and which comprises the insulin A-chain and B-chain.

EXAMPLES

Hereinafter, the present invention will be described in further detail with reference to examples. It will be obvious to a person having ordinary skill in the art that these examples are for illustrative purposes only and are not to be construed to limit the scope of the present invention.

In examples below, an ABD-fused insulin analogue is used as the same meaning as that of the long-acting insulin analogue derivative in the present invention.

Example 1: Construction of ABD-Fused Insulin Expression Vector and Strain

Human insulin is synthesized as a form of pre-pro-insulin, the pre sequence is cleaved off in the endoplasmic reticulum, and the pro-insulin is processed in the Golgi body and the endoplasmic reticulum, thereby forming mature insulin. Based on this fact, in order to produce recombinant insulin by a process of expressing pro-insulin protein in *E. coli* and then removing the C-chain by trypsin treatment, pro-insulin was designed. In order to increase the efficiency of expression of pro-insulin in *E. coli* and the efficiency of purification, a fusion tag was inserted into the N-terminus, and codon optimization was performed.

The number of insulin sites to which an albumin-binding domain (ABD) may be fused is theoretically four. However, the N-terminus of the A-chain is a position important for the activity of insulin, and thus was excluded from the fusion positions. Although the N-terminus of the B-chain is important for the formation of an insulin hexamer, it was included in the fusion positions, because the activity of insulin could be maintained. If ABD is fused between B-chain and C-chain, it may have an effect on protein folding. Thus, the insulin construct was designed in either B-C-A order or A-C-B order as a candidate structure. Finally, gene structures for expression of the following three forms of ABD-fused insulin were designed:

NdeI-Fusion tag-B-chain-C-chain-A-chain-Linker-ABD-EcoRI,

NdeI-Fusion tag-ABD-Linker-B-chain-C-chain-A-chain-EcoRI, and

NdeI-Fusion tag-A-chain-C-chain-B-chain-Linker-ABD-EcoRI.

As an expression vector, a pJ401(DNA 2.0) vector was used. The vector was digested with the restriction enzymes NdeI and EcoRI, and then the DNA fragments were separated by electrophoresis on 1% agarose gel. The gene structures for expression of ABD fusion proteins and the DNA fragments obtained from the expression vector as described above were ligated to each other using T4 DNA ligase, thereby constructing plasmids. Next, each of the plasmids was transformed into E. coli BL21(DE3) by a calcium chloride method. Transformed strains having resistance to kanamycin were selected, and DNA was isolated therefrom. Whether the DNA would be properly inserted was determined by an analysis method based on restriction enzyme digestion.

When the gene was designed to have an NdeI-fusion tag-ABD-Linker-B-chain-C-chain-A-chain-EcoRI structure, it was determined not proper due to a very low protein refolding yield. In addition, when the gene was designed to have an NdeI-fusion tag-A-chain-C-chain-B-chain-Linker-ABD-EcoRI structure, the ABD-fused insulin had insulin activity, but it showed low refolding yield and enzyme treatment yield, thus it was deemed unsuitable as a method to make an active form of insulin. Therefore, among the three forms of ABD-fused insulin, the NdeI-fusion tag-B-chain-C-chain-A-chain-Linker-ABD-EcoRI structure was selected and used in a subsequent experiment.

Between the A-chain and the albumin-binding domain (ABD), a linker consisting of 1 to 6 repeats of a (GGGGS) sequence was inserted. In this case, when the linker was not introduced, the refolding yield was very low, but when a linker consisting of two or more repeats of the (GGGGS) sequence, there was not a significant difference in the refolding yield. Meanwhile, as n in the $(GGGGS)_n$ sequence increased, the rate of conversion to an active form of insulin by clostripain increased, but the in vivo pharmacokinetics of the insulin were not significantly influenced. Taking the above-described results together, the linker was designed to consiste of 2 to 4 repeats of the GGGGS sequence.

The amino acid sequences of each portions for the ABD-fused insulin used in the present invention are shown in Table 1 below.

TABLE 1

| | Sequence | Sequence ID No. |
|---|---|---|
| Fusion Tag | MATTSTGNSAHHHHHHSSGSAR | 1 |
| B chain | FVNQHLCGSHLVEALYLVCGEKGFFYTPKT | 2 |
| C chain | RREAEDLQVGQVELGGGPGAGSLQPLALEG SQLAR | 3 |
| A chain | GIVEQCCTSICSLYQLENYCN | 4 |
| Linker | GGGGSGGGGS | 5 |
| ABD | LAEAKEAANAELDSYGVSDFYKKLIDKAKT VEGVEALKDAILAALP | 6 |

Example 2: Construction of ABD-Fused Insulin Analogues Having Modified Insulin Amino Acid Sequences To produce insulin using recombinant E. coli, a process of converting pro-insulin to an active form by use of trypsin is necessary. However, trypsin cleaves di-basic amino acids with high efficiency and also cleaves single amino acids such as lysine (Lys) or arginine (Arg), making it difficult to produce the desired active form of insulin. In addition, the ABD sequence also includes a number of lysine (Lys) and arginine (Arg) residues, making it further difficult to produce desired ABD-fused insulin having activity by use of trypsin.

For this reason, clostripain was used as an enzyme capable of replacing trypsin in order to induce conversion to an active form. In this case, when clostripain reacted with ABD-fused insulin, cleavage of arginine (Arg) at position 22 of the insulin B-chain occurred. To solve this problem, position 22 of the B-chain was substituted with lysine (Lys). In this case, the cleavage at position 22 of the insulin B-chain by clostripain significantly decreased, and thus an active form of ABD-fused insulin could be effectively produced (FIG. 1).

In addition to the mutation as described above, additional mutations were introduced into the ABD-fused insulin in order to further increase the stability and in vivo half-life of the ABD-fused insulin. Five amino acids in each of the A-chain and the B-chain were substituted, and the substituted positions are shown in Table 2 below.

TABLE 2

| Analogue | Modified sequence |
|---|---|
| Analogue 1 | V→L at position 3 of A-chain |
| Analogue 2 | T→D at position 8 of A-chain |
| Analogue 3 | I→K at position 10 of A-chain |
| Analogue 4 | Y→E at position 14 of A-chain |
| Analogue 5 | Y→F at position 19 of A-chain |
| Analogue 6 | H→T at position 5 of B-chain |
| Analogue 7 | S→D at position 9 of B-chain |
| Analogue 8 | E→A at position 13 of B-chain |
| Analogue 9 | L→Q at position 17 of B-chain |
| Analogue 10 | F→S at position 24 of B-chain |
| Analogue 11 | No additional mutation in A-chain or B-chain |

Codon optimization for gene expression in E. coli was performed using the GeneArt algorithm, and genes were synthesized to have the substituted amino acids.

The plasmids constructed as described above were introduced into E. coli BL21 (DE3) in the same manner as described in Example 1, thereby constructing E. coli strains.

Example 3: Expression of ABD-Fused Insulin Analogues

For expression of ABD-fused insulin analogues, each of the recombinant *E. coli* strains was inoculated into 100 mL of LB medium and shake-cultured at 37° C. for 16 hours, and the cultures were used as seed cultures. 2 L of LB medium was added to a 7-L fermenter (New Brunswick BioFlo), sterilized, and then inoculated with the seed culture. Culture was performed under the conditions of temperature of 35° C., air flow rate of 3 vvm and stirring speed of 1,000 rpm, and the pH during the culture was maintained at 6.8 with ammonia and phosphoric acid. At the time point at which the carbon source in the medium was exhausted, feeding was started and at the same time, protein expression was induced with IPTG. Additional culture was performed for 10 hours after induction of the expression, and recombinant strains were recovered using a centrifuge.

Figure 2:
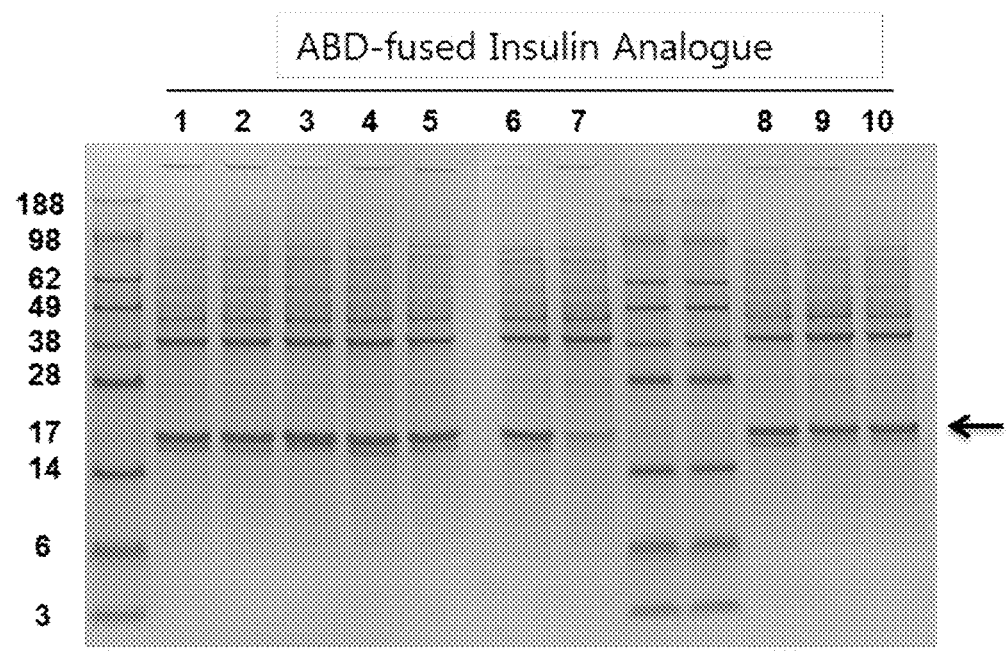
FIG. 2 shows the results of analyzing expression of long-acting insulin analogue derivatives 1 to 10 in recombinant E. coli by SDS-PAGE. Even when one or more mutations were introduced into the insulin sequence, protein expression in E. coli was retained.

The ABD-fused insulin analogues were expressed as inclusion bodies in the *E. coli* strain, and even when the amino acid mutations were introduced into the insulin domains, expression levels appeared in the vector system used in the present invention (FIG. 2).

Example 4: Induction of Cell Lysis and Solubilization/Refolding

Each of the strains expressing the ABD-fused insulin or the ABD-fused insulin analogues was suspended in lysis buffer (20 mM Tris, 10 mM EDTA, 10% sucrose, 0.2 M NaCl, pH 8.0), and the cells were lysed using a high-pressure homogenizer. The lysed cells were centrifuged in a high-speed centrifuge at 7,000 rpm, and soluble protein and some cell debris were removed, thereby isolating a precipitate including an inclusion body. The isolated inclusion body was washed with buffer (containing 1% Triton X-100, 0.2 M NaCl, and 1 M urea), and then centrifuged at 7,000 rpm. The precipitated inclusion body was additionally washed twice with distilled water, and was then stored at −80° C. until use.

Figure 3:
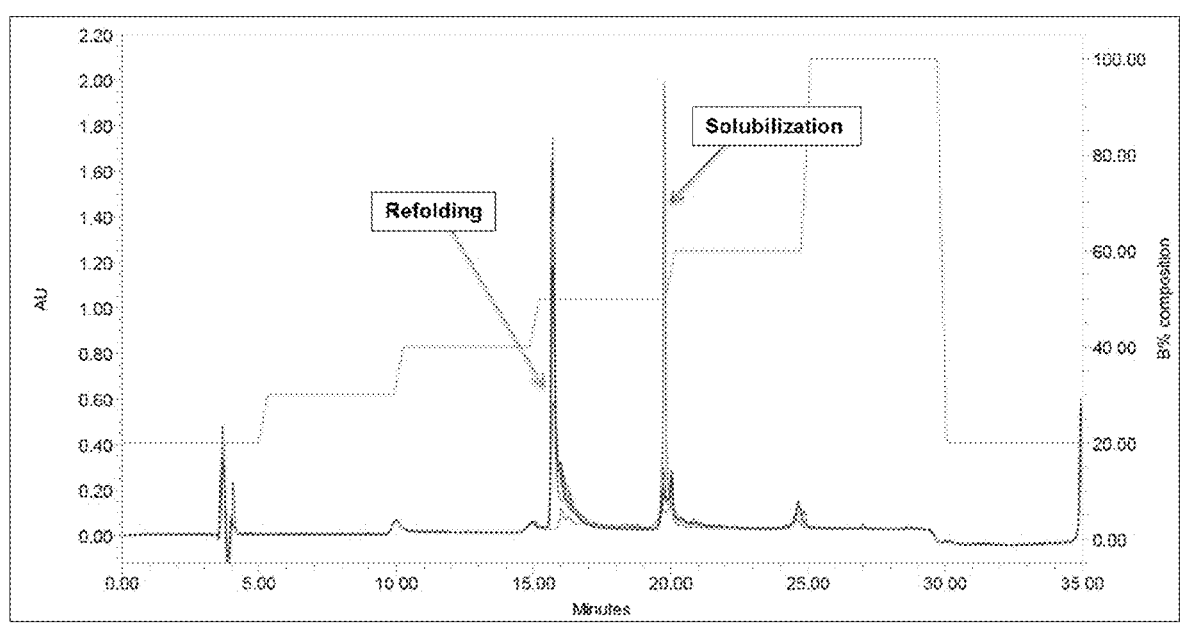
FIG. 3 shows the results of monitoring the solubilization and refolding of ABD-fused insulin analogue 4 by RP-HPLC. When the protein structure was unfolded by solubilization and followed by induction of refolding, the shift of retention time in RP-HPLC was observed due to formation of a three-dimensional structure.

The freeze-stored inclusion body was dissolved in solubilization buffer (25 mM Tris, 8 M Urea, 30 mM cysteine-HCl, pH 10.5), and then diluted in refolding buffer (25 mM Tris-HCl, pH 10.5), and subjected to refolding at 4° C. for 16 hours. Whether refolding would occur was determined by RP-HPLC analysis. When the solubilized solution was analyzed by RP-HPLC, the protein peak was observed at about 20 minutes due to high hydrophobicity, but when refolding proceeded, the shift of the peak to 16 minutes was observed (FIG. 3). This is because as the refolding progresses, the hydrophobicity decreases compared to that in the solubilized solution. The refolding was proceeded until the shift of the protein peak is not observed any more during the analysis by RP-HPLC.

Example 5: Conversion to Active Form by Use of Enzyme

For the production of insulin using a recombinant *E. coli* strain, the conversion of pro-insulin to an active form by use of trypsin is required. However, the ABD-fused insulin or the ABD-fused insulin analogue has a number of trypsin cleavage sites in its sequence, and for this reason, clostripain was used as an enzyme capable of replacing trypsin in order to induce conversion to an active form.

When conversion to an active form was induced using clostripain, cleavage at position 22 of the insulin B-chain occurred, making it difficult to produce a desired form of insulin. For this reason, an ABD-fused insulin analogue obtained by substituting position 22 of the B-chain from arginine (Arg) to lysine (Lys) was used to produce an active form of insulin. Meanwhile, ABD-fused insulin analogue 4 was used in all the experiments unless further specified.

Clostripain contains cysteine (Cys) in its active site, and thus requires reducing conditions in order to exhibit enzymatic activity. In addition, where a refolding solution is treated with a reducing agent in order to maintain clostripain activity, the disulfide bond in the insulin region is highly likely to be broken. For this reason, it is required to derive conditions that increase the enzymatic reaction yield without breaking the disulfide bond. Thus, using the reducing agent DTT contained in an enzymatic reaction solution, experiments on treatment concentration and additional treatment were performed.

In order to convert an ABD-fused insulin analogue in a precursor form to an active form, carboxypeptidase B (CpB) is also additionally required. The CpB is an enzyme that cleaves basic amino acids at the carboxyl terminus, and the detailed conditions thereof were also tested. Specifically, the time of treatment with clostripain and CpB, the possibility of simultaneous treatment, the amount of enzyme treatment, the temperature of enzyme treatment, and appropriate pH level were evaluated.

Because clostripain exists as a pro-form, auto-cleavage was induced to activate it. To this end, freeze-dried clostripain (Worthington, USA) was dissolved in distilled water, and then activated at 4° C. for 30 minutes after addition of activation buffer (500 mM Tris, 50 mM DTT, 25 mM CaCl$_2$) pH 7.8). The activated clostripain was added to the refolded protein at a concentration of 0.1 to 5 units per mg of the protein and allowed to react at 25 to 40° C. for 2 to 8 hours. After the clostripain reaction, CpB was added at a concentration of 0.001 to 1 unit per 1 mg of the protein and allowed to react. The enzymatic reaction was stopped by lowering the pH to 3.5 or less by use of HCl.

5-1: Evaluation of Efficiency of Conversion to Active Form after DTT Addition In order to examine enzymatic reaction conditions for clostripain and CpB, DTT was added to a refolding solution to a concentration of 0 to 0.4 mM, and then the production of an active form of insulin by clostripain was observed by SDS-PAGE. It was shown that when more than 0.5 mM of DTT was added, the disulfide bonds between the insulin A-chain and B-chain were broken (data not shown).

Figure 4:
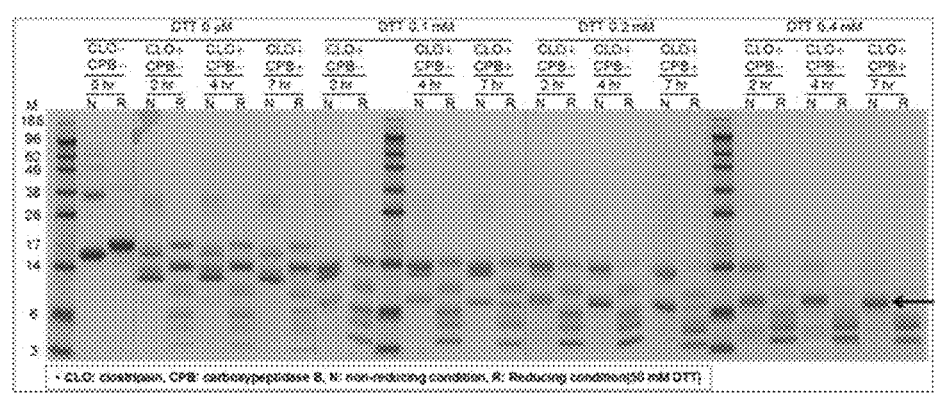
FIG. 4 shows the results of SDS-PAGE performed to analyze the production efficiency of an active form of ABD-fused insulin analogue 4 by clostripain treatment according to addition of DTT.

Meanwhile, as can be seen in FIG. 4, DTT was not added to the enzymatic reaction solution, the rate of conversion of the ABD-fused insulin analogue to an active form was low, but as the DTT concentration increased, the efficiency of conversion to the active form increased.

5-2: Evaluation of the Efficiency of Conversion to Active Form of Insulin at Various Time Points of Addition of CpB In order to convert the ABD-fused pro-insulin analogue to an active form, the pro-insulin analogue should be treated with both clostripain and CpB. In this regard, the time point of addition of CpB was determined. In order to cleave the insulin C-peptide and the fusion tag, treatment with clostripain should first be performed, and to remove arginine (Arg) from the cleaved site, treatment with CpB should then be performed. However, in order to shorten the production time, treatment with CpB at 2 to 4 hours after treatment with clostripain was compared with simultaneous treatment with clostripain and CpB.

Figure 5:
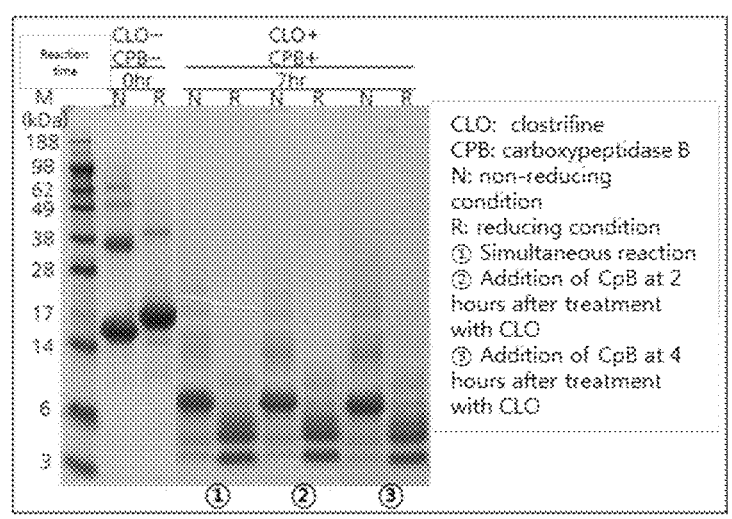
FIG. 5 shows the results of SDS-PAGE performed to analyze the efficiency of production of an active form of ABD-fused insulin analogue 4 according to the time of treatment with clostripain and CpB.

As a result, as can be seen in FIG. 5, the enzymatic reaction pattern in simultaneous treatment with clostripain and CpB did not differ from that in the condition in which treatment with clostripain is first performed. Thus, in order to improve the efficiency of the process, simultaneous treatment with clostripain and CpB was selected.

5-3: pH Conditions in Simultaneous Treatment with Clostripain and CpB

It is known that clostripain exhibits optimal activity at a pH of 7.4 to 7.8 and CpB exhibits optimal activity at a pH of 9.0. Because the optimal pH ranges of the two enzymes differ from each other, pH range showing the highest efficiency of conversion to an active form of insulin was determined by simultaneous treatment with the two enzymes. The theoretical pI values of all the ABD-fused insulin analogues shown in table 2 according to the present invention were close to 6, and thus precipitation was concerned. Accordingly, a pH of 6.0 or less was excluded. In addition, at a pH of 9.0 or more, an aggregate increased. For these reasons, evaluation was performed at a pH between 6.0 and 9.0.

Figure 6:
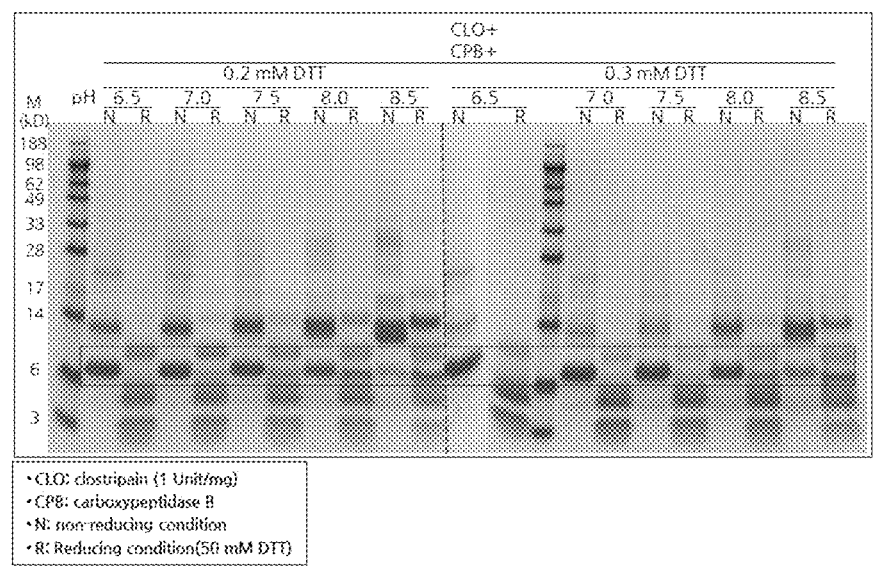
FIG. 6 shows the results of SDS-PAGE performed to determine the pH range in which an active form of ABD-fused insulin analogue 4 is produced with high efficiency upon simultaneous treatment with clostripain and CpB.

Simultaneous treatment with the two enzymes in the pH range of 6.5 to 8.5 showed a high efficiency of conversion to an active form of insulin. Besides, as shown in FIG. 6, the efficiency of conversion to an active form of insulin was particularly high in the pH range of 6.5 to 7.5.

5-4: Evaluation of the Efficiency of Conversion to Active Form of Insulin after Additional Addition of Clostripain and DTT As shown in Example 5-1, when DTT is added, the efficiency of conversion to an active form of insulin increases. However, the half-life of DTT is known to decrease rapidly at high pH and temperatures, and thus it was believed that it would be difficult to maintain the activity of clostripain in a long time of an enzymatic reaction. Accordingly, a method capable of maintaining the activity of clostripain for a long time was investigated.

Figure 7:
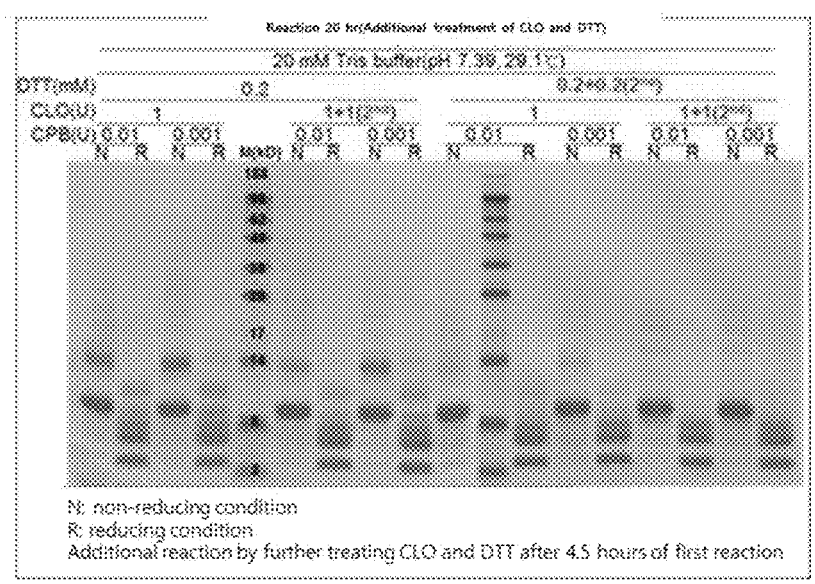
FIG. 7 shows the results of SDS-PAGE performed to analyze the production efficiency of an active form of ABD-fused insulin analogue 4 according to further addition of clostripain and DTT.

To this end, a method in which of 1 U/mg of clostripain is additionally added at 4.5 hours after the start of an enzymatic reaction was evaluated comparatively with a method in which 0.2 mM of DTT is additionally added. As a result, as shown in FIG. 7, even when clostripain was additionally added, the efficiency of conversion to an active form did not significantly increase, but when DTT was additionally added, conversion to an active form significantly increased even when clostripain was not additionally added. In addition, when both clostripain and DTT were additionally added, it was observed that the amount of an unconverted form was relatively small and the efficiency of conversion to an active form increased.

Figure 8:
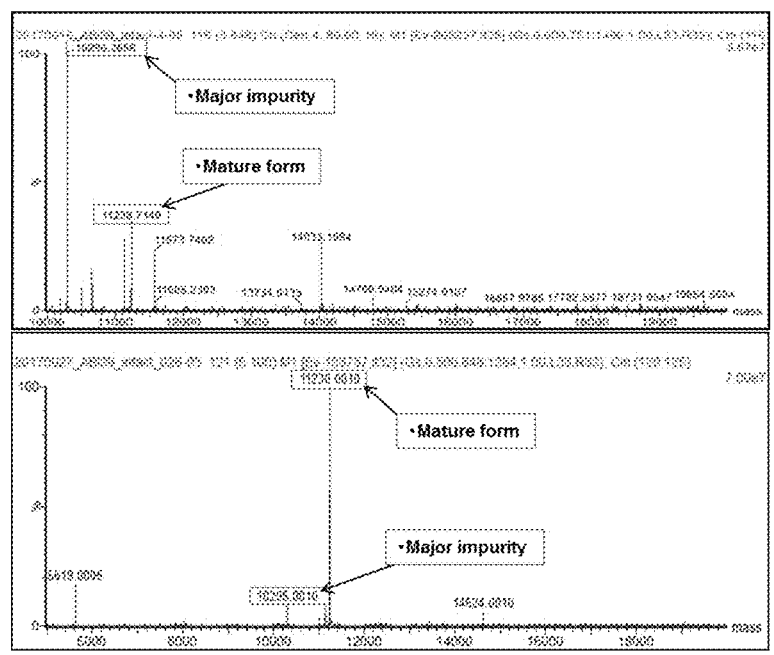
FIG. 8 shows the results of confirming the effects of increasing the efficiency of conversion to an active form of ABD-fused insulin analogue 4 and reducing impurities under optimal enzymatic reaction conditions according to an example of the present invention (molecular weight of major impurity: 10296 Da; molecular weight of active form of insulin: 11238 Da).

However, the analysis of the enzymatic reaction solution by mass spectrometry indicated that when DTT was added, conversion to an active form of insulin significantly increased, but when DTT and clostripain were simultaneously added, non-specific cleavage of insulin was rather induced, resulting in an increase in impurities. Thus, it could be seen that the addition of the reducing agent DTT alone would be advantageous for conversion to an active form of insulin (FIG. 8).

Figure 9:
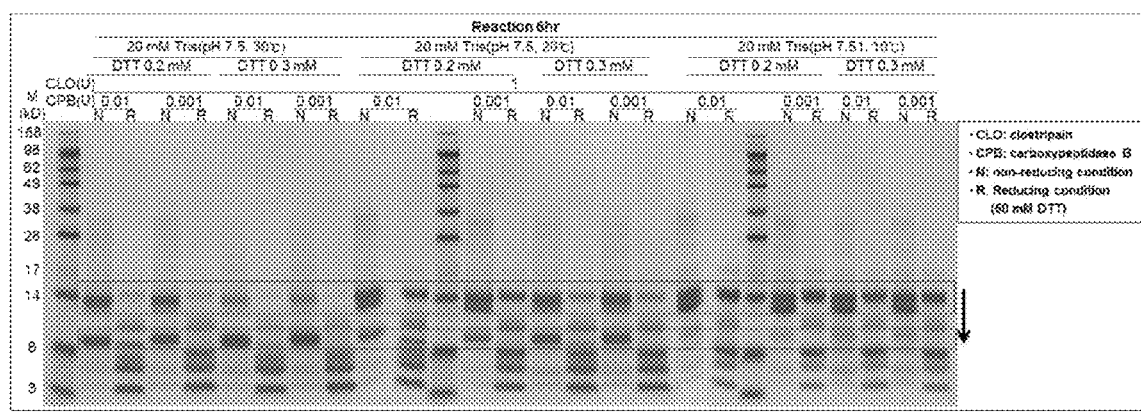
FIG. 9 shows the results of SDS-PAGE performed to determine the temperature range in which an active form of ABD-fused insulin analogue 4 is produced with high efficiency upon simultaneous treatment with clostripain and CpB.

5-5: Evaluation of Efficiency of Conversion to Active Form of Insulin at Various Temperatures An evaluation was performed to determine the temperature range in which clostripain and CpB would show optimal activities. At this time, considering the process operation at the production scale, a temperature of 4° C. or below and a temperature of 40° C. or above were excluded, and the evaluation was performed at a temperature of 10 to 30° C. As a result, as shown in FIG. 9, it could be seen that, as the temperature increased from 10° C. to 20° C. and 30° C., the amount of an unconverted form was smaller, and conversion to an active form proceeded faster. In addition, it was shown that, as the concentration of DTT increased, conversion to an active form proceeded faster.

Example 6: Purification of ABD-Fused Analogue Insulin

The sample enzymatically treated with clostripain and CpB was first purified by ion-exchange resin chromatography using Fractogel® EMD COO⁻ (M) (Merck) according to the manufacturer's instruction, and then further purified by reverse-phase chromatography using Pharmprep® P100 RP-18e (Merck) according to the manufacturer's instruction.

Figure 10:
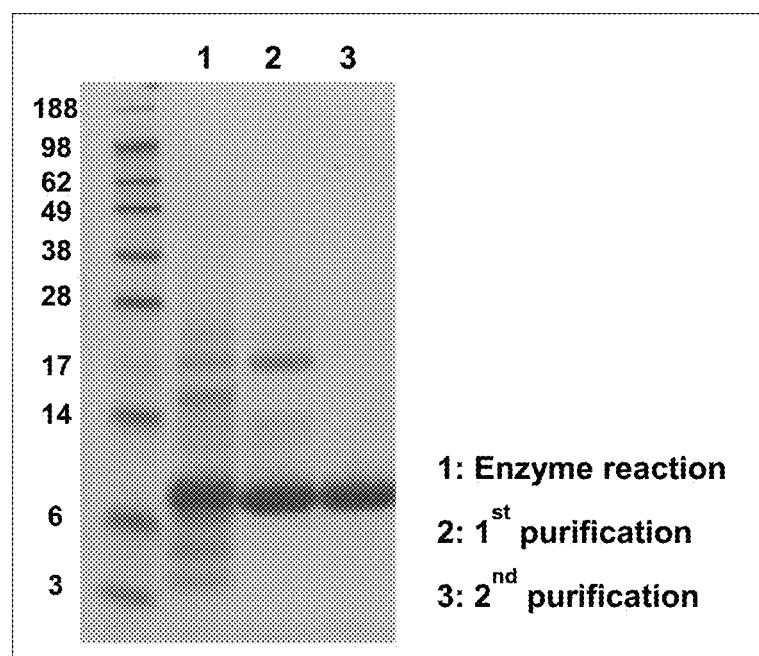
FIG. 10 shows the results of analyzing ABD-fused insulin analogue 4 by SDS-PAGE after digesting with clostripain and CpB and purifying it.

As a result, as can be seen in FIG. 10, an active form of impurity-free ABD-fused insulin analogue could be purified by the two purification processes.

Example 7: Measurement of the Binding Affinities of ABD-Fused Insulin Analogues for Albumin To measure the binding affinities of the ABD-fused insulin analogue proteins for albumin, a surface plasmon resonance (SPR, BIACORE 3000, GE healthcare) analysis method was used. Recombinant human serum albumin was immobilized on a CM5 chip by an amine coupling method, and the ABD or ABD-fused insulin analogues diluted to five or more concentrations were bound thereto, and the affinities thereof for the human serum albumin were measured.

As a result, as can be seen in Table 3 below, the affinities of the insulin analogues for the human serum albumin were maintained at pM levels, even though they were lower than that of the ABD itself.

TABLE 3

| Analogue | $K_a$ (1/Ms) | $K_d$ (1/s) | $K_D$ (M) |
| --- | --- | --- | --- |
| Analogue 1 | $4.54 \times 10^5$ | $2.37 \times 10^{-5}$ | $5.21 \times 10^{-11}$ |
| Analogue 2 | $4.42 \times 10^5$ | $3.14 \times 10^{-5}$ | $7.11 \times 10^{-11}$ |
| Analogue 3 | $2.51 \times 10^5$ | $4.36 \times 10^{-5}$ | $1.74 \times 10^{-10}$ |
| Analogue 4 | $4.64 \times 10^5$ | $3.32 \times 10^{-5}$ | $7.17 \times 10^{-11}$ |
| Analogue 5 | $3.26 \times 10^5$ | $3.13 \times 10^{-5}$ | $9.6 \times 10^{-11}$ |
| Analogue 6 | $3.27 \times 10^5$ | $4.75 \times 10^{-5}$ | $1.45 \times 10^{-10}$ |
| Analogue 7 | $7.87 \times 10^5$ | $5.26 \times 10^{-5}$ | $6.68 \times 10^{-11}$ |
| Analogue 8 | $3.7 \times 10^5$ | $6.46 \times 10^{-5}$ | $1.75 \times 10^{-10}$ |
| Analogue 9 | $4.77 \times 10^5$ | $3.76 \times 10^{-5}$ | $7.9 \times 10^{-11}$ |
| Analogue 10 | $6.25 \times 10^5$ | $4.23 \times 10^{-5}$ | $6.77 \times 10^{-11}$ |
| ABD | $5.93 \times 10^6$ | $2.41 \times 10^{-5}$ | $7.29 \times 10^{-12}$ |

Example 8: Comparison of the Affinities of Native Insulin and ABD-Fused Insulin Analogues for Insulin Receptor To measure the binding affinities of native insulin and ABD-fused insulin analogues for insulin receptor, a surface plasmon resonance (SPR, BIACORE 3000, GE healthcare) analysis method was used. Insulin receptor was immobilized on a CM5 chip by an amine coupling method, and each of native insulin and ABD-fused insulin analogues, diluted to five or more concentrations, was bound thereto, and the affinities thereof for the insulin receptor were measured.

As a result, as can be seen in Table 4 below, the affinities of the ABD-fused insulin analogues were reduced compared to that of native insulin. In particular, the affinity of analogue 3 showed the greatest reduction and fell to a level of about 19.4% relative to native insulin.

TABLE 4

| Analogue | $K_a$ (1/Ms) | $K_d$ (1/s) | $K_D$ (M) |
| --- | --- | --- | --- |
| Analogue 1 | $8.54 \times 10^4$ | — | — |
| Analogue 2 | $4.38 \times 10^4$ | $3.15 \times 10^{-3}$ | $7.2 \times 10^{-8}$ |
| Analogue 3 | $2.52 \times 10^4$ | $2.18 \times 10^{-3}$ | $8.65 \times 10^{-8}$ |
| Analogue 4 | $2.82 \times 10^4$ | $1.31 \times 10^{-3}$ | $4.65 \times 10^{-8}$ |
| Analogue 5 | $4.07 \times 10^4$ | $2.34 \times 10^{-3}$ | $5.75 \times 10^{-8}$ |
| Analogue 6 | $5.23 \times 10^4$ | $2.27 \times 10^{-3}$ | $4.33 \times 10^{-8}$ |
| Analogue 7 | $5.05 \times 10^4$ | — | — |
| Analogue 8 | $4.86 \times 10^4$ | $1.47 \times 10^{-3}$ | $3.04 \times 10^{-8}$ |
| Analogue 9 | $2.13 \times 10^4$ | $1.29 \times 10^{-3}$ | $6.06 \times 10^{-8}$ |
| Analogue 10 | $3.83 \times 10^4$ | — | — |
| Insulin | $1.03 \times 10^5$ | $1.72 \times 10^{-3}$ | $1.68 \times 10^{-8}$ |

The efficacies of the ABD-fused insulin analogues were evaluated comparatively with that of insulin glargine in type 1 diabetic models induced by streptozotocin. Analogues 1, 3 and 10 were excluded from the candidates since they showed a blood glucose lowering ability of 50% or less compared to insulin glargine.

Example 9: Hexamer Synthesis

Figure 11:
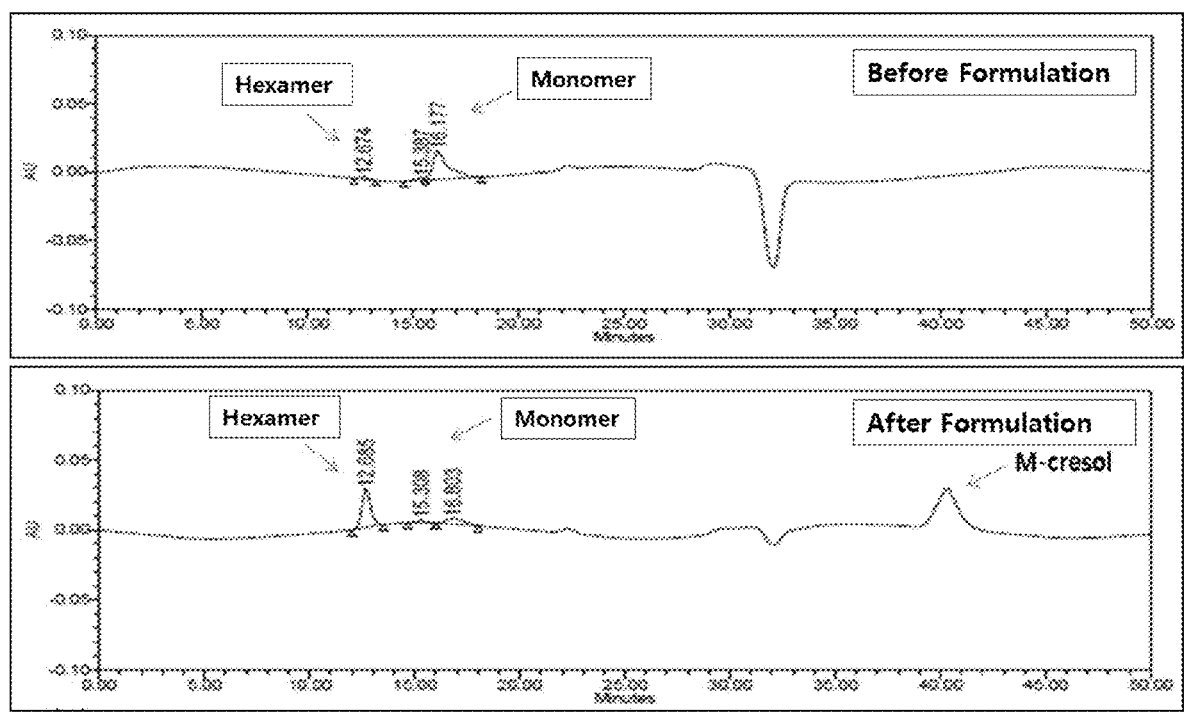
FIG. 11 shows the results of size-exclusion chromatography analysis performed to examine whether a hexamer would be formed when zinc and phenol were added to ABD-fused insulin analogue 4 according to an example of the present invention.

Insulin binds to zinc in vivo, thereby forming a stable hexamer structure. The insulin's property of forming a hexamer is also used in formation development and may play an important role in increasing the in vivo half-life of insulin. Accordingly, whether the ABD-fused insulin analogues would retain the property of forming hexamers was analyzed by size-exclusion chromatography. As a result, it was shown that analogue 4 retained the ability to form a hexamer by addition of zinc and phenol (FIG. 11). The formation of the hexamer was also observed in all the analogues excluding analogues 7, 9 and 10. Thus, among the analogues having the sequences shown in Table 2, analogues 7 and 9 were further excluded from candidates.

Example 10: Evaluation of In Vivo Pharmacokinetics and Blood Glucose Lowering Ability of ABD-Fused Insulin Analogues To evaluate the in vivo pharmacokinetics of the six ABD-fused insulin analogues, each of the insulin analogues was administered subcutaneously to normal SD rats (6-week old), and then blood was sampled at 0, 1, 4, 8, 24, 48, 72 and 96 hours. The concentration of each ABD-fused insulin analogue remaining in the blood at each of the time points was measured using ELISA. In addition, using a portion of the sampled blood, time-dependent blood glucose levels were measured with a blood glucose monitoring device.

As a result, as can be seen in Table 5 below, the ABD-fused insulin analogues showed significantly increased half-lives compared to native insulin known to have a half-life of minutes. Analogue 11 obtained by substituting only position 22 of the insulin B-chain showed a half-life of 7.2 hours, and analogue 4 showing the greatest increase in half-life was evaluated to have a half-life of 9.9 hours.

Figure 12:
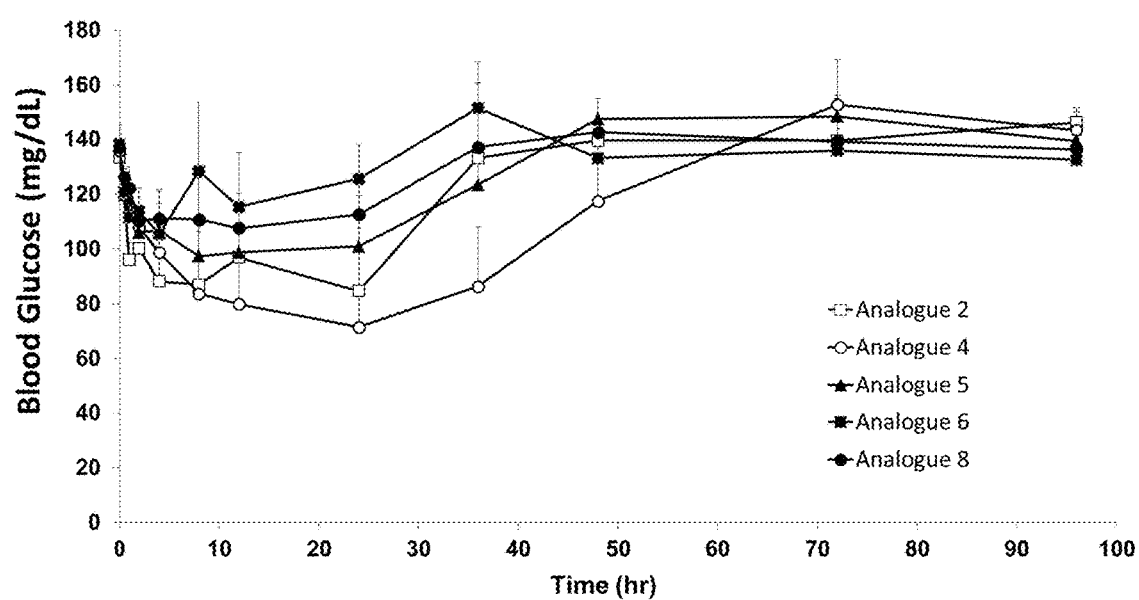
FIG. 12 shows the results of evaluating the blood glucose lowering ability of ABD-fused insulin analogues according to an example of the present invention.

The time during which blood glucose levels in the normal animals were maintained at reduced levels was analyzed. As a result, it was shown that analogues 5, 6 and 8 had increased half-lives, but maintained blood glucose levels for a short time. In comparison with these analogues, analogue 4 had the best ability to lower blood glucose levels and maintained its efficacy for the longest time (FIG. 12).

TABLE 5

| Parameter | Analogue 2 | Analogue 4 | Analogue 5 | Analogue 6 | Analogue 8 | Analogue 11 |
| --- | --- | --- | --- | --- | --- | --- |
| $T_{1/2}$ (hr) | 9.4 ± 3.4 | 9.9 ± 0.1 | 9.1 ± 0.7 | 8.4 ± 1.7 | 8.8 ± 0.4 | 7.2 ± 2.3 |
| MRT (hr) | 17.0 ± 2.2 | 22.1 ± 1.3 | 21.2 ± 0.3 | 15.9 ± 1.5 | 19.8 ± 1.5 | 16.3 ± 0.9 |

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

In a conventional method of converting proinsulin to an active form by use of trypsin, an albumin binding domain of the novel long-acting insulin analogue derivative, newly developed by the present inventors, is also cleaved, thus making it difficult to convert the novel long-acting insulin analogue derivative into an active form. To overcome this difficulty, clostripain was used for converting the insulin analogue derivative according to the present invention to an active form. Thus, the method of the present invention may be effectively used for the production of the long-acting therapeutic agent for treatment of diabetes.

The invention claimed is:

1. A method for producing an active form of a long-acting insulin analogue derivative, the method comprising
a step of reacting an insulin analogue derivative with clostripain,
wherein the insulin analogue derivative comprises an insulin B-chain variant, an insulin C-chain, an insulin A-chain or variant thereof, a linker and an albumin-binding domain in that order,
wherein the insulin-B chain variant represented by the amino acid sequence of SEQ ID NO: 2, arginine (Arg) at amino acid position 22 of an insulin-B chain is substituted with lysine (Lys) in native insulin.

2. The method of claim 1, wherein the insulin analogue further comprises one or more amino acid substitutions selected from the group consisting of:
a valine (Val)-to-leucine (Leu) substitution at amino acid position 3 of an insulin A-chain represented by the amino acid sequence of SEQ ID NO: 4;
a threonine (Thr)-to-aspartic acid (Asp) substitution at amino acid position 8 of the insulin A-chain represented by the amino acid sequence of SEQ ID NO: 4;
an isoleucine (Ile)-to-lysine (Lys) substitution at amino acid position 10 of the insulin A-chain represented by the amino acid sequence of SEQ ID NO: 4;
a tyrosine (Tyr)-to-glutamic acid (Glu) substitution at amino acid position 14 of the insulin A-chain represented by the amino acid sequence of SEQ ID NO: 4;
a tyrosine (Tyr)-to-phenylalanine (Phe) substitution at amino acid position 19 of the insulin A-chain represented by the amino acid sequence of SEQ ID NO: 4;
a histidine (His)-to-threonine (Thr) substitution at amino acid position 5 of an insulin B-chain variant represented by the amino acid sequence of SEQ ID NO: 2;
a serine (Ser)-to-aspartic acid (Asp) substitution at amino acid position 9 of the insulin B-chain variant represented by the amino acid sequence of SEQ ID NO: 2;
a glutamic acid (Glu)-to-alanine (Ala) substitution at amino acid position 13 of the insulin B-chain variant represented by the amino acid sequence of SEQ ID NO: 2;
a leucine (Leu)-to-glutamine (Gln) substitution at amino acid position 17 of the insulin B-chain variant represented by the amino acid sequence of SEQ ID NO: 2; and
a phenylalanine (Phe)-to-serine (Ser) substitution at amino acid position 24 of the insulin B-chain variant represented by the amino acid sequence of SEQ ID NO: 2.

3. The method of claim 1, wherein the albumin-binding domain comprises an albumin-binding motif represented by the following amino acid sequence:
GVSDFYKKLIX$_a$KAKTVEGVEALKX$_b$X$_c$I
wherein
X$_a$ is independently selected from D and E,
X$_b$ is independently selected from D and E, and
X$_c$ is independently selected from A and E.

4. The method of claim 3, wherein the albumin-binding domain comprises the following amino acid sequence:
LAX$_3$AKX$_6$X$_7$ANX$_{10}$ELDX$_{14}$Y-[BM]-LX$_{43}$X$_{44}$LP
wherein
[BM] is an albumin-binding motif as defined in claim 3,
X$_3$ is independently selected from C, E, Q, and S;
X$_6$ is independently selected from C, E, and S;
X$_7$ is independently selected from A and S;
X$_{10}$ is independently selected from A, R, and S;
X$_{14}$ is independently selected from A, C, K, and S;
X$_{43}$ is independently selected from A and K; and
X$_{44}$ is independently selected from A, E, and S.

5. The method of claim 4, wherein the albumin-binding domain is represented by an amino acid sequence selected from the group consisting of SEQ ID NOS: 6 to 13.

6. The method of claim 5, wherein the albumin-binding domain is represented by the amino acid sequence of SEQ ID NO: 6.

7. The method of claim 1, wherein the insulin analogue and the albumin-binding domain are fused to each other by a peptide bond; a polypeptide linker; or a non-peptidyl linker selected from the group consisting of polyethylene glycol, polypropylene glycol, an ethylene glycol-propylene glycol copolymer, polyoxyethylated polyol, polyvinyl alcohol, polysaccharides, dextran, polyvinyl ethyl ether, biodegradable polymers, fatty acids, nucleotides, lipid polymers, chitin, hyaluronic acid, and combinations thereof.

8. The method of claim 7, wherein the polypeptide linker comprises (GGGGS)$_n$ wherein n is an integer ranging from 1 to 6.

9. The method of claim 8, wherein the polypeptide linker is represented by the amino acid sequence of SEQ ID NO: 5.

10. The method of claim 1, wherein a reducing agent is added during the reaction with clostripain.

11. The method of claim 10, wherein the reducing agent is selected from the group consisting of cysteine, β-mercaptoethanol, TCEP (Tris(2-carboxyethyl)phosphine hydrochloride), GSH (Glutathione) and DTT (Dithiothreitol).

12. The method of claim 10, wherein 0.1 to 0.5 mM of DTT is added as the reducing agent.

13. The method of claim 12, wherein the DTT is added at an initial stage in which the insulin analogue derivative reacts with clostripain, and is further added at 3 to 6 hours after the reaction.

14. The method of claim 1, wherein the insulin analogue derivative is further reacted with carboxypeptidase B (CpB) which is added during or after the reaction with clostripain.

15. The method of claim 14, wherein the clostripain and/or carboxypeptidase B (CpB) are/is reacted under the conditions of pH 6.0-9.0.

16. The method of claim 15, wherein the clostripain and/or carboxypeptidase B (CpB) are/is reacted under the conditions of pH 6.5-7.5.

17. The method of claim 14, wherein the clostripain and/or carboxypeptidase B (CpB) are/is reacted under the conditions of 4-40° C.

18. An active form of a long-acting insulin analogue derivative produced by the method of claim 1.

* * * * *

UNITED STATES PATENT AND TRADEMARK OFFICE
CERTIFICATE OF CORRECTION

PATENT NO. : 11,655,279 B2
APPLICATION NO. : 17/266580
DATED : May 23, 2023
INVENTOR(S) : Kyong Hoon Ahn It is certified that error appears in the above-identified patent and that said Letters Patent is hereby corrected as shown below:

In the Specification

Column 9, Line 13, "racy" should be -- rac5 --.

Signed and Sealed this
Fourth Day of July, 2023

Katherine Kelly Vidal
*Director of the United States Patent and Trademark Office*

SEQUENCE LISTING

<160> NUMBER OF SEQ ID NOS: 13

<210> SEQ ID NO 1
<211> LENGTH: 22
<212> TYPE: PRT
<213> ORGANISM: Artificial Sequence
<220> FEATURE:
<223> OTHER INFORMATION: Synthetic construct

<400> SEQUENCE: 1

Met Ala Thr Thr Ser Thr Gly Asn Ser Ala His His His His His His
1               5                   10                  15

Ser Ser Gly Ser Ala Arg
            20

<210> SEQ ID NO 2
<211> LENGTH: 30
<212> TYPE: PRT
<213> ORGANISM: Artificial Sequence
<220> FEATURE:
<223> OTHER INFORMATION: Synthetic construct

<400> SEQUENCE: 2

Phe Val Asn Gln His Leu Cys Gly Ser His Leu Val Glu Ala Leu Tyr
1               5                   10                  15

Leu Val Cys Gly Glu Lys Gly Phe Phe Tyr Thr Pro Lys Thr
            20                  25                  30

<210> SEQ ID NO 3
<211> LENGTH: 35
<212> TYPE: PRT
<213> ORGANISM: Artificial Sequence
<220> FEATURE:
<223> OTHER INFORMATION: Synthetic construct

<400> SEQUENCE: 3

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Ala Arg
        35

<210> SEQ ID NO 4
<211> LENGTH: 21
<212> TYPE: PRT
<213> ORGANISM: Artificial Sequence
<220> FEATURE:
<223> OTHER INFORMATION: Synthetic construct

<400> SEQUENCE: 4

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5

```
Gly Gly Gly Gly Ser Gly Gly Gly Ser
1               5               10
```

<210> SEQ ID NO 6
<211> LENGTH: 46
<212> TYPE: PRT
<213> ORGANISM: Artificial Sequence
<220> FEATURE:
<223> OTHER INFORMATION: Synthetic construct

<400> SEQUENCE: 6

```
Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
                20                  25                  30

Gly Val Glu Ala Leu Lys Asp Ala Ile Leu Ala Ala Leu Pro
            35                  40                  45
```

<210> SEQ ID NO 7
<211> LENGTH: 46
<212> TYPE: PRT
<213> ORGANISM: Artificial Sequence
<220> FEATURE:
<223> OTHER INFORMATION: Synthetic construct

<400> SEQUENCE: 7

```
Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
                20                  25                  30

Gly Val Glu Ala Leu Lys Asp Glu Ile Leu Ala Ala Leu Pro
            35                  40                  45
```

<210> SEQ ID NO 8
<211> LENGTH: 46
<212> TYPE: PRT
<213> ORGANISM: Artificial Sequence
<220> FEATURE:
<223> OTHER INFORMATION: Synthetic construct

<400> SEQUENCE: 8

```
Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
                20                  25                  30

Gly Val Glu Ala Leu Lys Glu Ala Ile Leu Ala Ala Leu Pro
            35                  40                  45
```

<210> SEQ ID NO 9
<211> LENGTH: 46
<212> TYPE: PRT
<213> ORGANISM: Artificial Sequence
<220> FEATURE:
<223> OTHER INFORMATION: Synthetic construct

<400> SEQUENCE: 9

```
Leu Ala Glu Ala Lys Glu Ala Ala Asn Ala Glu Leu Asp Ser Tyr Gly
1               5                   10                  15

Val Ser Asp Phe Tyr Lys Lys Leu Ile Asp Lys Ala Lys Thr Val Glu
                20                  25                  30

Gly Val Glu Ala Leu Lys Glu Glu Ile Leu Ala Ala Leu Pro
            35                  40                  45
```

<210> SEQ ID NO 10
<211> LENGTH: 46
<212> TYPE: PRT
<213> ORGANISM: Artificial Sequence
<220> FEATURE:
<223> OTHER INFORMATION: Synthetic construct

<400> SEQUENCE: 10

Leu Ala Glu Ala Lys Glu Ala Ala Asn Ala Glu Leu Asp Ser Tyr Gly
1               5                   10                  15

Val Ser Asp Phe Tyr Lys Lys Leu Ile Glu Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 11
<211> LENGTH: 46
<212> TYPE: PRT
<213> ORGANISM: Artificial Sequence
<220> FEATURE:
<223> OTHER INFORMATION: Synthetic construct

<400> SEQUENCE: 11

Leu Ala Glu Ala Lys Glu Ala Ala Asn Ala Glu Leu Asp Ser Tyr Gly
1               5                   10                  15

Val Ser Asp Phe Tyr Lys Lys Leu Ile Glu Lys Ala Lys Thr Val Glu
            20                  25                  30

Gly Val Glu Ala Leu Lys Asp Glu Ile Leu Ala Ala Leu Pro
        35                  40                  45

<210> SEQ ID NO 12
<211> LENGTH: 46
<212> TYPE: PRT
<213> ORGANISM: Artificial Sequence
<220> FEATURE:
<223> OTHER INFORMATION: Synthetic construct

<400> SEQUENCE: 12

Leu Ala Glu Ala Lys Glu Ala Ala Asn Ala Glu Leu Asp Ser Tyr Gly
1               5                   10                  15

Val Ser Asp Phe Tyr Lys Lys Leu Ile Glu Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 13
<211> LENGTH: 46
<212> TYPE: PRT
<213> ORGANISM: Artificial Sequence
<220> FEATURE:
<223> OTHER INFORMATION: Synthetic construct

<400> SEQUENCE: 13

Leu Ala Glu Ala Lys Glu Ala Ala Asn Ala Glu Leu Asp Ser Tyr Gly
1               5                   10                  15

Val Ser Asp Phe Tyr Lys Lys Leu Ile Glu Lys Ala Lys Thr Val Glu
            20                  25                  30

Gly Val Glu Ala Leu Lys Glu Glu Ile Leu Ala Ala Leu Pro
        35                  40                  45